(12) United States Patent
Herbert-Guillou et al.

(10) Patent No.: US 6,856,937 B2
(45) Date of Patent: Feb. 15, 2005

(54) METHOD AND DEVICE FOR DETECTING A BIOFILM

(75) Inventors: Delphine Herbert-Guillou, Saint Julien (FR); Dominique Festy, Saint Renan (FR); Bernard Tribollet, Malakoff (FR); Laurent Kiene, Andresy (FR)

(73) Assignee: Ondeo Services (FR)

( * ) Notice: Subject to any disclaimer, the term of this patent is extended or adjusted under 35 U.S.C. 154(b) by 65 days.

(21) Appl. No.: 10/169,863

(22) PCT Filed: Jan. 9, 2001

(86) PCT No.: PCT/FR01/00056
§ 371 (c)(1),
(2), (4) Date: Sep. 6, 2002

(87) PCT Pub. No.: WO01/51913
PCT Pub. Date: Jul. 19, 2001

(65) Prior Publication Data
US 2003/0132144 A1 Jul. 17, 2003

(30) Foreign Application Priority Data
Jan. 10, 2000 (FR) .............................. 00 00228

(51) Int. Cl.[7] .............................................. B01D 35/00
(52) U.S. Cl. ................................................... 702/170
(58) Field of Search .................. 702/170; 429/43; 427/38; 524/257, 434; 204/296; 502/129; 523/210; 210/640

(56) References Cited

U.S. PATENT DOCUMENTS

| | | | |
|---|---|---|---|
| 4,059,406 A | 11/1977 | Fleet | |
| 4,565,919 A | 1/1986 | Berger | |
| 4,789,434 A | 12/1988 | Little et al. | |
| 5,334,292 A | * 8/1994 | Rajeshwar et al. | ......... 205/419 |
| 6,059,943 A | * 5/2000 | Murphy et al. | ............. 204/296 |
| 2002/0012821 A1 | * 1/2002 | Leddy et al. | ................. 429/10 |

* cited by examiner

*Primary Examiner*—John Barlow
*Assistant Examiner*—Tung Lau
(74) *Attorney, Agent, or Firm*—Connolly, Bove, Lodge & Hutz LLP

(57) ABSTRACT

A method for determining the thickness of a biofilm which is developed on a support which is immersed in an aqueous medium in which a biofilm develops, characterized in that it consists in the following: a) the medium is continuously circulated in an electrochemical cell comprising a reference electrode, an auxiliary electrode and at least one working electrode, b) circulation of said medium is interrupted and the cell is isolated; c) an electrochemical tracer is introduced into the medium present in the cell; d) the medium/tracer solution is circulated in the cell in order to direct a jet of said solution, perpendicular to the working electrode; e) the value of the tracer reduction limiting current is measured and recorded according to the hydrodynamic conditions on the surface of the working electrode; and f) the thickness of the porous layer of biofilm on the surface of the electrode is calculated according to the Koutecky-Levich relation, based on analysis of the transport of material through the porous layer which links the value of the tracer reduction limiting current to the solution flow.

2 Claims, 4 Drawing Sheets

METHOD AND DEVICE FOR DETECTING A BIOFILM

FIELD OF THE INVENTION

The present invention relates to a method and a device for determining the thickness of a biofilm.

BACKGROUND OF THE INVENTION

It is known that, especially in the field of water treatment, fixed culture techniques are employed in which the ability of microorganisms to produce exopolymers enabling them to be fixed to very diverse supports in order to form biofilters is used. Although, in these applications, the properties of the biofilms are exploited beneficially to remove contaminants (nitrates, phosphates, etc.), on the other hand, the same biofilms are often undesirable, or even detrimental. Thus, in some industrial plants immersed in aqueous media, the development of microorganisms, bacteria and algae, which are deposited on the plants in the form of biofilms, constitutes real microbiological pollution and the prevention and control of the growth of these biofilms require implementing relatively sophisticated, efficient and expensive techniques, the most common of which is chlorination.

Optimization of the treatments (improving performance, removing waste, reducing costs) is related to the possibility of determining the growth rate of the biofilms in real time.

At present, methods making it possible to detect the presence of biofilms and which have been the subject of industrial development are few. In order to illustrate the prior art in this field mention may especially be made of the following publications.

U.S. Pat. Nos. 4,912,332 and 5,337,376 relate to a method of detecting microbiological pollution using optical fibres. This known technique is based on measuring transmitted and absorbed light in order to monitor the formation of the biofilms. It has the drawback of being difficult to use in pipes.

U.S. Pat. No. 5,576,481 describes a method of detecting on-line biofilms based on measuring the heat transfer coefficient. The change in the latter is directly related to the development of the biofilm.

An apparatus making it possible to identify the biofilms and to control the use of biodispersants, which uses the conventional method of measuring the adenosine triphosphate is known by the brand "Bioscan". This apparatus has in particular the following drawbacks: on the one hand, the measurement depends on the bacterial cells sampled in the medium studied and not on the biofilm itself and, on the other hand, it is complicated and expensive.

Another sensor for monitoring the biofilm, called "BIoGEORGE" is known, which consists of two stainless steel electrodes, mounted on a body also made of stainless steel, and a data control and acquisition system. The measurement is based on analysing the change in current flowing between the two electrodes, after interruption by a galvanostatic prepolarization. This change is correlated to the presence of the biofilm and to the type of corrosion products on the surface of the electrodes. Given that the interaction between the biofilm and the stainless steels is very complex, detection of the biofilm alone seems very difficult with this sensor and, in addition, the measurements can only be carried out in seawater.

The "BioX" sensor records the value of the galvanic coupling current between a stainless steel and a copper alloy which is associated with the growth phase of the biofilm.

The "BioGuard" sensor, based on the electrochemical detection of the catalysis for the reduction of oxygen by bacteria, makes it possible to monitor the first steps in the formation of the biofilm.

B. N. Stokes et al ("Developments in on-line fouling and corrosion surveillance" published in "Microbiologically influenced corrosion testing" in 1994 by J. R. Keans and B. Little, Philadelphia, USA) have developed a device enabling corrosion and fouling to be monitored having the form of a miniaturized heat exchanger in which the corrosion is monitored by a measurement using an ammeter with zero resistance, a measurement of the electrochemical noise (current/potential) and a measurement of the linear polarization resistance, while fouling is detected by measuring the heat transfer coefficient. The use of these four electrochemical techniques makes the system complex and not very adaptable on site.

G. Salvago et al ("Biofilm monitoring and on-line control: 20-month experience in seawater" published in 1994 in "Microbiol Corrosion" by the European Federation of Corrosion) have studied the behaviour of stainless steels and of aluminium brasses exposed to seawater. The combination of the heat transfer resistance and of the electrochemical measurements under cathodic polarization enables the growth of a biofilm on the inner surface of tubes to be monitored. The various techniques used in such a system make it complex.

Experience demonstrates that all the currently known biofilm detectors have the drawback of being complex in their use. The present invention therefore set itself the objective of providing a biofilm sensor making it possible to measure the thickness of the biofilm and which can be used in various media (seawater, freshwater, water from industrial processes, etc.).

According to the present invention, the ability of a given medium to develop a biofilm when travelling around a circuit is assessed by electrochemical means by using a sensor based on the principle of the electrochemical cell with three electrodes.

Firstly, and according to a first aspect, this invention aims to provide a method of determining the thickness of a biofilm developing on a support immersed in an aqueous medium where such a biofilm is developing, characterized in that it consists in:

a) continuously circulating the said medium in an electrochemical cell comprising a reference electrode, an auxiliary electrode and at least one working electrode;

b) interrupting the circulation of the said medium and isolating the cell;

c) introducing an electrochemical tracer in the medium present in the cell;

d) circulating the medium+tracer solution in the said cell so as to direct a jet of the said solution perpendicularly to the working electrode;

e) measuring and recording the value of the limiting current for reducing the said tracer, as a function of the hydrodynamic conditions at the surface of the working electrode, and f) calculating the thickness of the porous biofilm layer at the surface of the said electrode by applying the Koutecky-Levich equation, based on analysing the transport of matter through the porous layer which relates the value of the limiting current for reducing the tracer to the flowrate of the solution.

With regard to the Koutecky-Levich equation, reference may be made to the article by D. Herbert-Guillou et al published in Electrochimica Acta, 1999, Vol. 4, No. 7, page 1067.

BRIEF DESCRIPTION OF THE INVENTION

According to a second aspect, the invention also aims to provide a method of determining the thickness of a biofilm developing on a support immersed in an aqueous medium where such a biofilm is developing, characterized in that it consists in:

a) continuously circulating the said medium in an electrochemical cell comprising a reference electrode, an auxiliary electrode and at least one working electrode;

b) interrupting the circulation of the said medium and isolating the cell;

c) circulating, in the said cell, the said medium in which oxygen is normally dissolved and which functions as an electrochemical tracer, so as to direct a jet of the said medium perpendicularly to the working electrode;

d) measuring and recording the value of the limiting current for reducing the oxygen dissolved in the medium, as a function of the hydrodynamic conditions at the surface of the working electrode, and e) calculating the thickness of the porous biofilm layer at the surface of the said electrode by applying the Koutecky-Levich equation, based on analysing the transport of matter through the porous layer which relates the value of the limiting current for reducing the tracer to the flowrate of the solution.

Thus according to the inventive method, the value of the limiting current for reducing an electrochemical tracer, which can for example be the oxygen present in the medium or potassium ferricyanide introduced into the medium contained in the cell before the measurement, as a function of the hydrodynamic conditions at the surface of the working electrode, is recorded. The Koutecky-Levich equation based on analysing the transport of matter through a porous layer relates the value of the limiting current for reducing the tracer to the flowrate of the electrolytic solution (medium+ tracer) and makes it possible to calculate the thickness of the porous layer at the surface of the working electrode.

Secondly, the invention aims to provide a device for implementing the method defined above which is characterized in that it comprises:

an electrochemical cell fitted with a reference electrode, a counter electrode and at least one working electrode, the said cell defining a chamber receiving the pipes for supply and discharge of the medium to be studied, with the insertion of solenoid valves;

a recycling loop in which the electrolytic solution consisting of the medium to be studied, to which the electrochemical tracer has been added, or in which the naturally dissolved oxygen acts as an electrochemical tracer, circulates continuously during the measurement;

a set of nozzles, each one placed opposite a working electrode in order to direct a jet of the electrolytic solution perpendicularly onto the said electrodes;

a variable capacity pump on the said recycling loop, and instrumentation for measuring the thickness of the biofilm which is deposited on the working electrodes during the circulation of the medium to be studied through the cell.

Other characteristics and advantages of the invention will become apparent from the description given below of an exemplary embodiment of the invention given by way of non-limiting example with reference to the drawings in which:

DETAILED DESCRIPTION OF THE INVENTION

Figure 1:
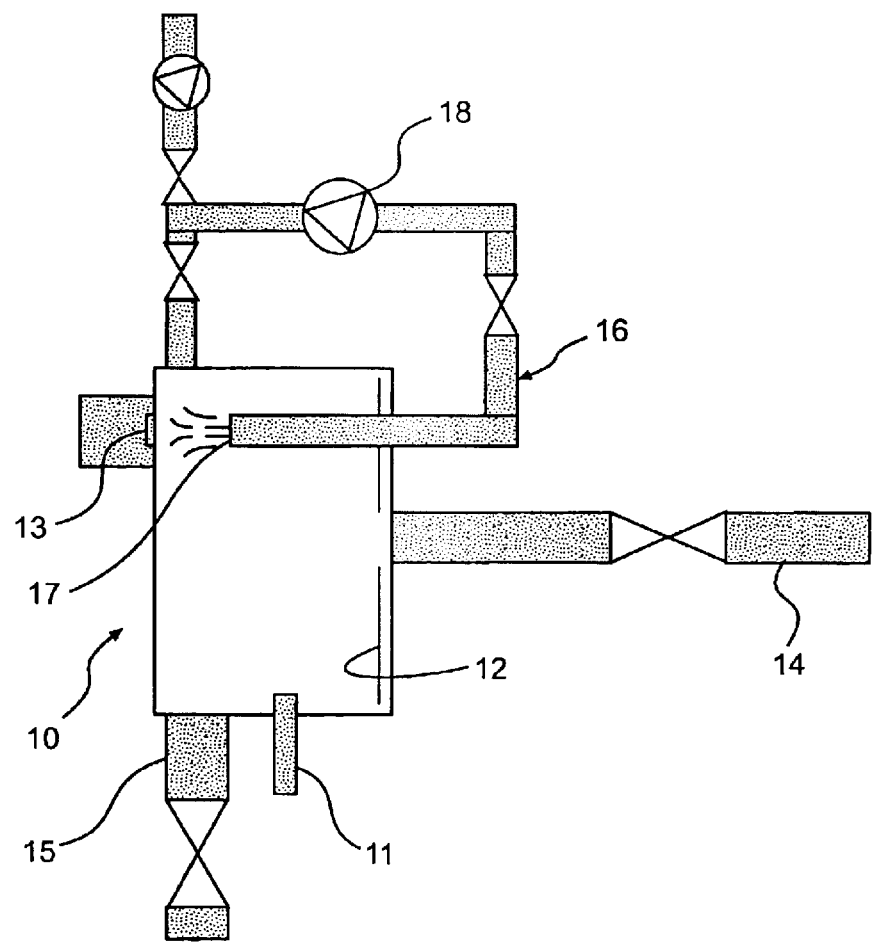
FIG. 1 is a schematic representation of the device according to the invention.
Figure 2:
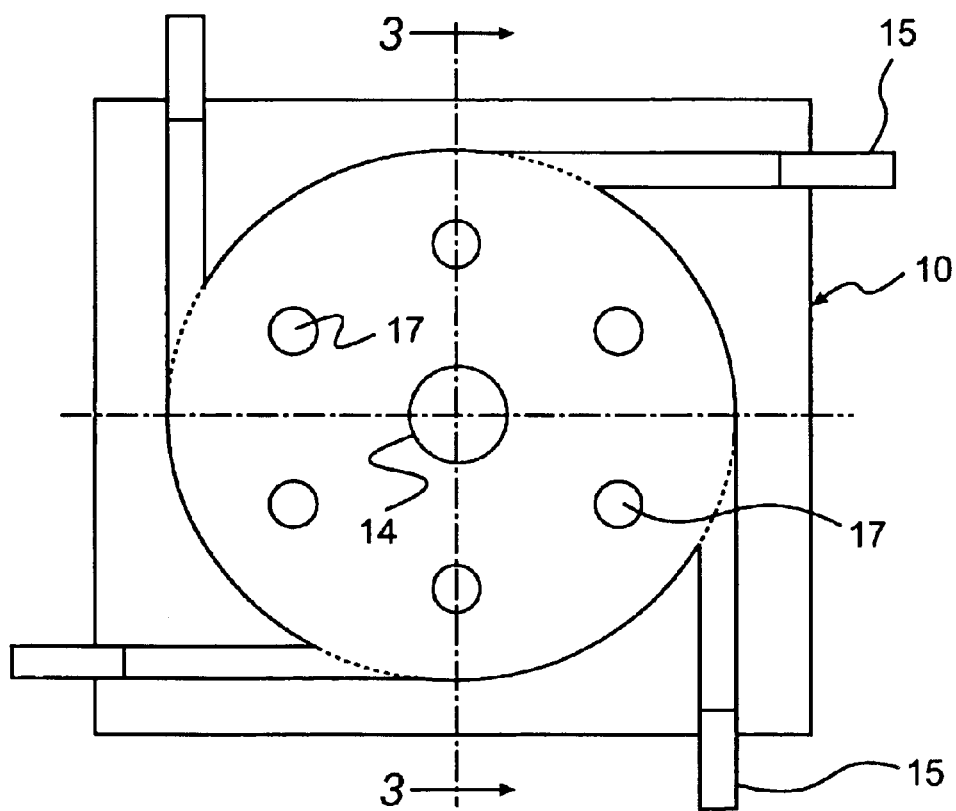
FIGS. 2 and 3 are schematic views in plan and in section along 3-3 of FIG. 2 of a sensor according to the invention.
Figure 3:
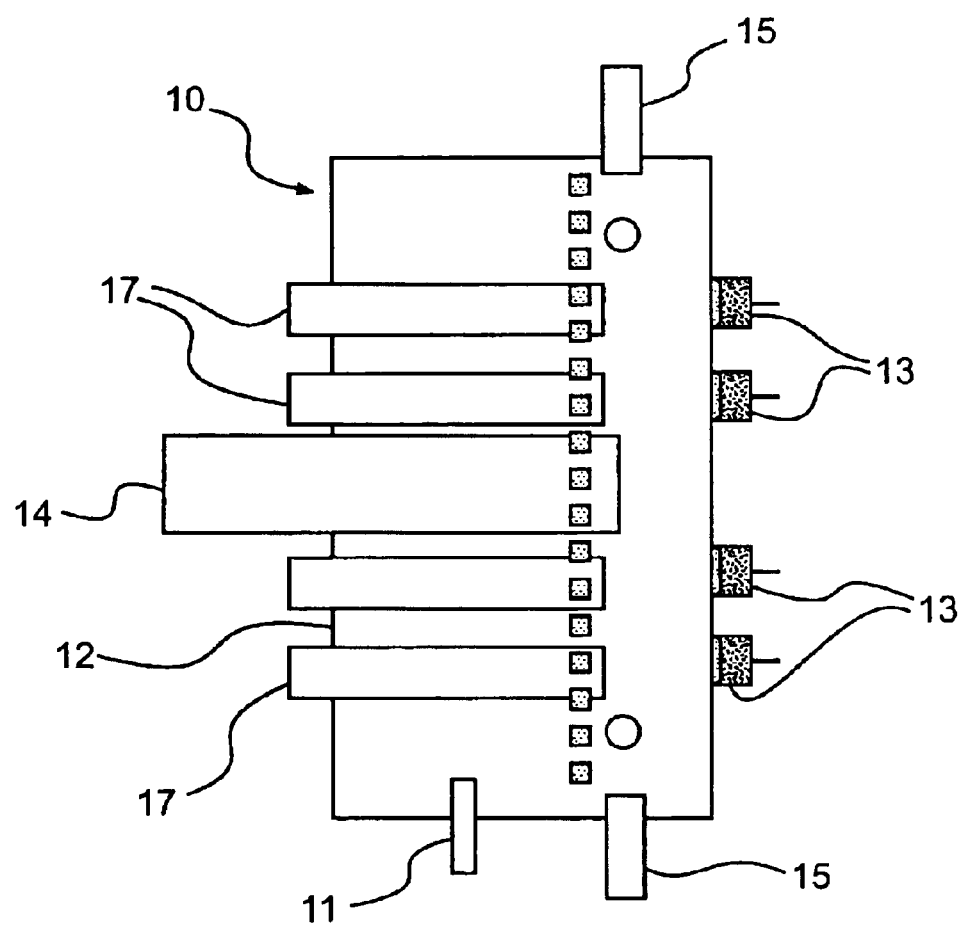

With reference to FIGS. 1 to 3, it can be seen that, in this exemplary embodiment, the device according to the invention comprises an electrochemical cell, denoted overall by the reference 10, which comprises a reference electrode 11, a counter electrode 12 and working electrodes such as 13. In this exemplary embodiment, six working electrodes are provided in order to overcome the spatial heterogeneity of the biofilm. The electrodes preferably consist of the following materials:

reference electrode 11: calomel (Hg/Hg$_2$Cl$_2$)

counter electrode 12: platinized platinum, working electrodes 13: gold.

The medium to be studied, in particular seawater, freshwater or water from an industrial process, is introduced into the cell via a central nozzle 14 and it emerges therefrom via pipes such as 15, solenoid valves being provided on these inlets and outlets.

A closed-loop circuit 16 is linked to the cell 10. The electrochemical tracer is introduced into this circuit and the electrolytic solution (medium+tracer) continuously circulates by virtue of a variable capacity pump 18. As can be seen in FIG. 1, the solenoid valves enable the loop 16 to be put out of service when the sensor is not used for measuring the thickness of the biofilm. The loop circuit 16 opens out into the cell via nozzles such as 17 facing each working electrode 13 so as to direct a jet with a variable flowrate of the electrolytic solution perpendicularly onto the said electrodes.

The device is completed by instrumentation such as a potentiostat and multimeter for measuring the thickness of the biofilm layer on the working electrodes such as 13.

This device is implemented as follows:

1) circulating the medium studied in the cell 10, 2) measurement at t=0 with no biofilm on the working electrodes, a) stopping the circulation of the medium, isolating the cell by closing the solenoid valves on the pipes for supply and discharge of the medium;

b) polarizing the selected working electrode (13) at a predetermined potential;

c) bringing the variable capacity pump 18 into service after having introduced the electrochemical tracer into the loop 16; stabilizing the flowrate; measuring the current; changing the value of the flowrate of the pump 18, a new current measurement; repeating this cycle for a predetermined number of times;

d) shutting down the variable capacity pump;

e) stopping the polarization of the electrode;

f) passing to the following working electrode; repeating the previous cycle on this electrode.

3) bringing the medium back into circulation in the cell by opening the solenoid valves on the introduction 14 and discharge 15 pipes. Taking the loop 16 out of service.

4) at regular intervals:

a) resuming the cycle 2;

b) calculating the thickness of the biofilm deposited on the working electrodes 13.

5) bringing the medium back into circulation.

Figure 4:
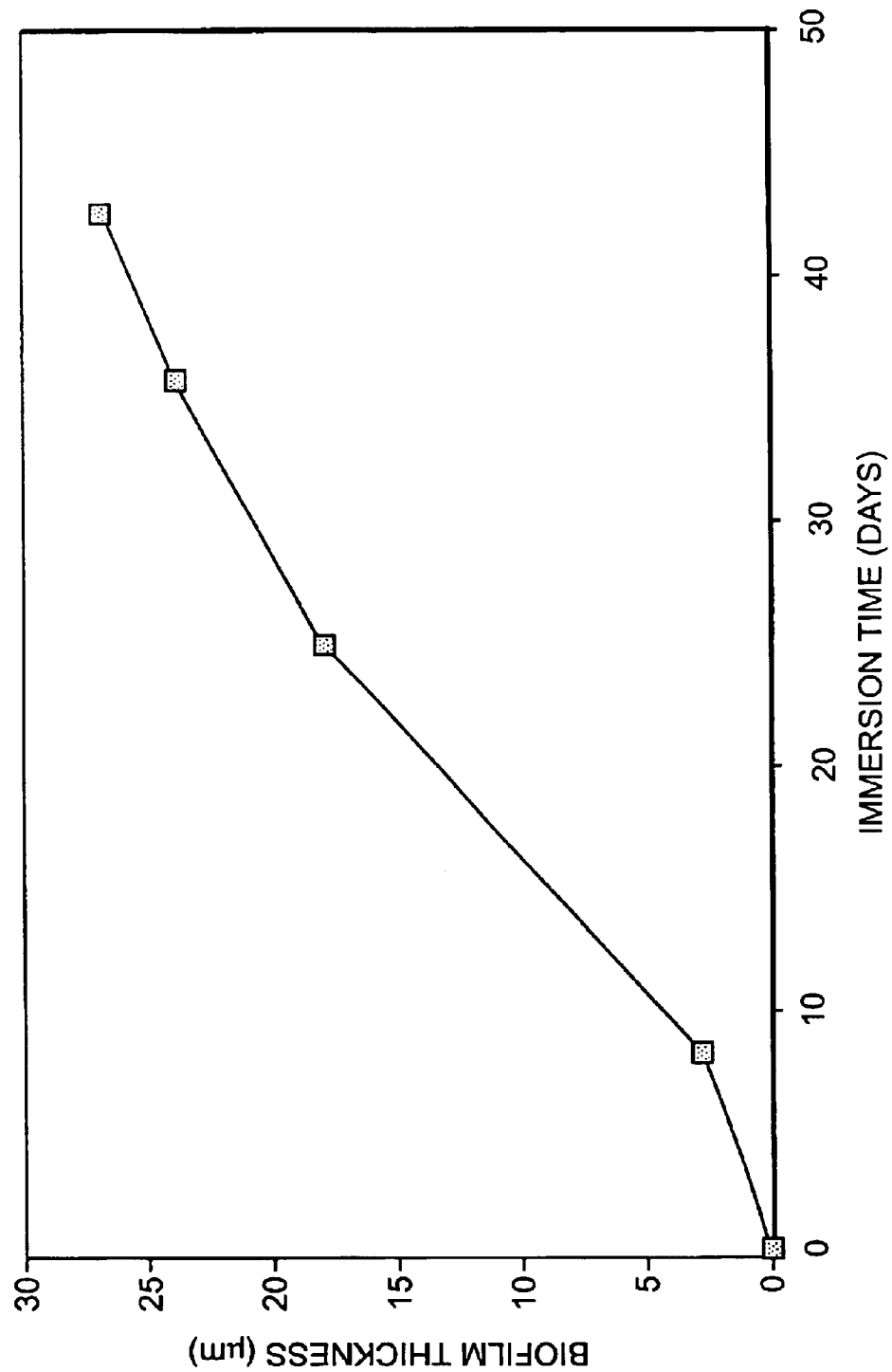
FIG. 4 illustrates the mean thickness of a biofilm obtained in natural seawater, for a flowrate of 6 ml.s$^{-1}$, as a function of immersion time.

The sensor according to the invention has made it possible to monitor the change in thickness of the biofilm during ageing in natural seawater for a period of forty-three days. After eight days of immersion, a biofilm of a few micrometers thick was detected on the electrodes, reaching several tens of micrometers after forty-three days. The curve illustrated in FIG. 4 illustrates the variation of the mean thickness of the biofilm thus obtained as a function of the immersion time, for a circulation flowrate of 6 ml.s$^{-1}$.

It results from reading the above description that the invention provides a device which is simple, inexpensive and easy to use, making it possible to measure the thickness of the biofilm in different media.

Of course it remains that the invention is not limited to the exemplary embodiments and/or the implementational examples described and/or shown but that it encompasses all variants.

What is claimed is:

1. A method of determining the thickness of a biofilm developing on a support immersed in an aqueous medium where such a bioflim is developing, comprising the steps:
    a) continuously circulating the medium in an electrochemical cell comprising a reference electrode, an auxiliary electrode and at least one working electrode;
    b) interrupting the circulation of the medium and isolating the cell;
    c) introducing an electrochemical tracer in the medium present in the cell;
    d) circulating the medium+tracer solution in the cell so as to direct a let of the solution perpendicularly to the working electrode;
    e) measuring and recording the value of the limiting current for reducing the tracer, as a function of the hydrodynamic conditions at the surface of the working electrode;
    f) calculating the thickness of the porous bioflim layer at the surface of the electrode by applying the Koutecky-Levich equation, based on analyzing the transport of matter through the porous layer which relates the value of the limiting current for reducing the tracer to the flowrate of the solution; and
    wherein the electrochemical tracer is potassium ferricyanide.

2. A method of determining the thickness of a biofilm developing on a support immersed in an aqueous medium where such a biofilm is developing, comprising the steps:
    a) continuously circulating the medium in an electrochemical cell comprising a reference electrode, an auxiliary electrode and at least one working electrode;
    b) interrupting the circulation of the medium arid isolating the cell;
    c) introducing an electrochemical tracer in the medium present in the cell;
    d) circulating the medium+tracer solution in the cell so as to direct a jet of the solution perpendicularly to the working electrode;
    e) measuring and recording the value of the limiting current for reducing the tracer, as a function of the hydrodynamic conditions at the surface of the working electrode;
    f) calculating the thickness of the porous bioflim layer at the surface of the electrode by applying the Koutecky-Levich equation, based on analyzing the transport of matter through the porous layer which relates the value of the limiting current for reducing the tracer to the flowrate of the solution;

an electrochemical cell fitted with a reference electrode, a counter electrode and at least one working electrode, the cell defining a chamber receiving pipes for supply and discharge of the medium to be studied, with the insertion of solenoid valves;

a recycling loop in which the electrolytic solution consisting of the medium to be studied, to which the electrochemical tracer has been added, or of the medium itself in which the naturally dissolved oxygen acts as a tracer, circulates continuously during the measurement;

a set of nozzles, each one placed opposite a working electrode in order to direct a jet of the electrolytic solution perpendicularly onto the electrodes;

a variable capacity pump on the recycling loop, and instrumentation for measuring the thickness of the biofilm which is deposited on the working electrodes during the circulation of the medium to be studied through the cell.

* * * * *

UNITED STATES PATENT AND TRADEMARK OFFICE
CERTIFICATE OF CORRECTION

PATENT NO. : 6,856,937 B2
DATED : February 15, 2005
INVENTOR(S) : Delphine Herbert-Guillou et al.

It is certified that error appears in the above-identified patent and that said Letters Patent is hereby corrected as shown below:

Column 5,
Line 22, "bioflim" should read -- biofilm --;
Line 31, "let" should read -- jet --;
Line 38, "bioflim" should read -- biofilm --;

Column 6,
Line 7, "arid" should read -- and --;
Line 18, "bioflim" should read -- biofilm --.

Signed and Sealed this

Twenty-fourth Day of May, 2005

JON W. DUDAS
*Director of the United States Patent and Trademark Office*